(12) United States Patent  
Legallois et al.

(10) Patent No.: US 9,271,761 B2  
(45) Date of Patent: Mar. 1, 2016

(54) BONE ANCHORING DEVICE

(71) Applicant: Zimmer Spine, Bordeaux (FR)

(72) Inventors: Georges Legallois, Bordeaux (FR); Karl Belliard, La Membrolle sur Longuenee (FR); Nicolas Bidegaimberry, Gradigan (FR); Thomas Bouvry, Champhol (FR)

(73) Assignee: Zimmer Spine, Bordeaux (FR)

( * ) Notice: Subject to any disclaimer, the term of this patent is extended or adjusted under 35 U.S.C. 154(b) by 0 days.

(21) Appl. No.: 13/803,178

(22) Filed: Mar. 14, 2013

(65) Prior Publication Data

US 2014/0163618 A1     Jun. 12, 2014

(51) Int. Cl.
    *A61B 17/88*     (2006.01)
    *A61B 17/70*     (2006.01)

(52) U.S. Cl.
    CPC ........... *A61B 17/7037* (2013.01); *A61B 17/704* (2013.01)

(58) Field of Classification Search
    CPC ........... A61B 17/7032; A61B 17/7037; A61B 17/70; A61B 17/7002; A61B 17/7085; A61B 17/7035; A61B 17/708; A61B 17/88; A61B 17/7011; A61B 17/7049; A61B 17/705; A61B 17/7091; A61B 17/701; A61B 17/7055
    USPC .................. 606/250–279, 300, 301, 305–308
    See application file for complete search history.

(56) References Cited

U.S. PATENT DOCUMENTS

| | | | |
|---|---|---|---|
| 7,625,396 B2 * | 12/2009 | Jackson ........................ | 606/305 |
| 7,875,065 B2 | 1/2011 | Jackson | |
| 2006/0129149 A1 * | 6/2006 | Iott et al. ........................ | 606/61 |
| 2008/0161853 A1 | 7/2008 | Arnold et al. | |
| 2008/0161863 A1 | 7/2008 | Arnold et al. | |
| 2008/0243193 A1 * | 10/2008 | Ensign et al. ................. | 606/305 |
| 2010/0298891 A1 * | 11/2010 | Jackson ......................... | 606/308 |
| 2011/0093021 A1 * | 4/2011 | Fanger et al. ................. | 606/308 |
| 2012/0165882 A1 | 6/2012 | Biedermann et al. | |
| 2012/0265257 A1 | 10/2012 | Jackson | |
| 2012/0303063 A1 | 11/2012 | Cahill et al. | |
| 2014/0236238 A1 | 8/2014 | Ark et al. | |
| 2014/0243900 A1 | 8/2014 | Ark et al. | |

FOREIGN PATENT DOCUMENTS

| | | |
|---|---|---|
| EP | 2769692 A1 | 8/2014 |
| GB | 2483531 A | 3/2012 |
| WO | 2006089292 A2 | 8/2006 |

OTHER PUBLICATIONS

International Search Report for Corresponding Application No. PCT/EP2013/075864.

* cited by examiner

*Primary Examiner* — Mary Hoffman  
*Assistant Examiner* — Tara R Carter  
(74) *Attorney, Agent, or Firm* — Schwegman Lundberg & Woessner, P.A.

(57) ABSTRACT

A bone anchoring device for securement to a bone. The device includes an anchor, a receiver, a retainer and an insert. The receiver includes a seating surface defining a cavity communicating with the exterior of the receiver through a first opening configured to receive the connection head of the anchor therethrough. The retainer includes at least two discrete retaining members configured to engage with the receiver seating surface when they are captured between the connection head and the seating surface. The insert is disposed within the receiver and configured to frictionally engage the connection head. The insert includes a main body and at least one pin protruding from the main body, for circumferential insertion between two adjacent retaining members of the retainer.

21 Claims, 3 Drawing Sheets

FIG.5  FIG.6  FIG.7 ly to the diameter of a
circular opening or the diameter of a cylindrical or spherical
member.

BONE ANCHORING DEVICE

CROSS-REFERENCE TO RELATED APPLICATIONS

This application claims priority to EP 12306561.7, filed on Dec. 11, 2012, the entire disclosure of which is incorporated herein by reference.

FIELD OF THE INVENTION

The present disclosure relates generally to bone anchoring devices. Bone anchoring devices may be helpful for holding together a bone and a support member in a desired configuration.

BACKGROUND OF THE INVENTION

One field of application for the disclosed bone anchoring device is holding together a bone, e.g. a vertebra, and a support member, e.g. a rod, in a desired relative position, while allowing in some cases a limited amount of relative movement, for example to aid in healing of breaks or to correct bony structure deficiencies and abnormalities. In particular, sufferers of abnormal spine curvature or other spine deficiencies may benefit from the disclosed bone anchoring device.

When the spine of a person has abnormal curvature or other deficiencies, e.g. a damaged intervertebral disc, vertebrae usually need to be stabilized in a correct position relative to one another.

A common technique for providing vertebral stabilization is to fix bone anchors, such as pedicle screws or hooks, to certain vertebrae, the bone anchors being then, in turn, fixed to a support member, usually an elongate structure such as a rod. The rod connects the anchors together, thereby providing stabilization between the vertebrae.

U.S. Pat. No. 5,005,562 discloses a bone screw having a threaded shank to be anchored into the bone and a fixed head formed integrally with the shank, the fixed head having a U-shaped slot for receiving a rod. This so-called monoaxial bone screw has a high resistance to loads. However, the screw head cannot be moved relative to the shank and the rod or the bone screw must be favorably positioned in order for the rod to be placed within the U-shaped slot. This may be sometimes very difficult to do.

For this reason, polyaxial bone screws may be preferred. Polyaxial bone screws allow rotation of the head, or receiver, about the threaded shank until a desired rotational position of the receiver is achieved relative to the shank. Thereafter, a rod can be inserted into the receiver and eventually the receiver is locked or fixed in a particular position relative to the threaded shank.

U.S. Pat. No. 7,875,065 discloses an example of a polyaxial bone screw. This screw comprises a shank having a threaded portion topped by a shank head, a receiver for receiving the shank head and a retainer structure comprising two discrete pieces. The retainer pieces totally circumferentially surround the shank head and are captured between the receiver and the shank head. As shown in FIGS. 6 to 8 of U.S. Pat. No. 7,875,065, for assembling the bone screw, the retainer pieces are first top-loaded into the receiver, passed therethrough and placed in the bottom thereof. Then, the shank head is bottom-loaded into the receiver, between the two retainer pieces. However, placing the retainer pieces in their right position may present practical difficulties and take time. Moreover, misplacement of the retainer pieces may make the shank head difficult to insert between them. Furthermore, in the disclosed embodiments, the shank head is non-spherical and articulation occurs between the retainer pieces and the receiver.

While polyaxial bone anchoring devices and, in particular, polyaxial bone screws have proven effective, further improvements, especially regarding their assembly and handling, would be beneficial.

SUMMARY OF THE INVENTION

According to one aspect of the present disclosure, there is provided a bone anchoring device comprising:
an anchor comprising a connection head and a bone anchoring part for fixation to a bone,
a receiver having a top portion and a base, the base having a seating surface defining a cavity, the cavity communicating with an exterior of the receiver through a first opening at a lower end of the receiver, the first opening being configured to receive the connection head therethrough,
a retainer structure, or retainer, comprising at least two discrete retaining members, the retaining members being configured to fit into the receiver seating surface when they are captured between the connection head and the seating surface, and
an insert disposed within the receiver and configured to frictionally engage the connection head.

The first opening of the receiver has a cross-sectional dimension greater than the maximum cross-sectional dimension of the connection head, i.e. is dimensioned such that the connection head fits through and may be guided through the first opening, and has a cross-sectional dimension smaller than the maximum cross-sectional dimension of the cavity.

In the frame of the present disclosure a cross-sectional dimension shall be understood as a linear dimension measured across an opening, a cavity or a body, and the skilled person will readily recognize that this is e.g. the diameter of a circular opening or the diameter of a cylindrical or spherical member.

While the connection head is freely movable through the first opening of the receiver the retainer may be designed such that, when fit into the cavity, it captures the connection head within the receiver, at least against displacement towards the bottom of the receiver.

The bone anchoring part of the anchor may be a threaded shank, a hook or have any other appropriate shape for anchoring, and the connection head may be integral with the bone anchoring part. Since the connection head is bottom-loaded into the receiver cavity, through the first opening, the dimensions of the bone anchoring part may exceed the dimensions of the first opening. Thus, the size and shape of the bone anchoring part can be freely chosen depending, for instance, on the bone on which the anchoring part is to be fixed. This allows the use of a broad range of anchoring part sizes without the need of enlarging the receiver size.

In an exemplary embodiment, the insert comprises a main body configured to frictionally engage the connection head and at least one pin, or spacer, protruding from the main body, each pin being configured for circumferential insertion between two adjacent retaining members of the retainer, so as to hold these retaining members circumferentially spaced apart from each other thus securing the retaining members inside the cavity. Thus, the pin impedes relative movement between the retaining members, thereby improving the mechanical behavior of the device, while reducing the risk that the retaining members disengage from the receiver. In addition, when the insert is blocked in rotation with respect to the receiver, the pin impedes, in turn, the rotation of the retaining members relative to the receiver. Typically, when the retainer comprises two retaining members, the insert comprise two pins on opposite sides of the main body.

The insert may be movable relative to the receiver, along a first axis, and the main body of the insert and, more particularly, the lower surface of the main body may be configured to exert a force onto the connection head, thus clamping the connection head between the insert and a lower edge of the retainer.

In the present disclosure, the axial direction corresponds to the direction of the first axis, i.e. the movement direction of the insert, and a radial direction is a direction perpendicular to the first axis. Similarly, an axial plane is a plane containing the first axis and a radial plane is a plane perpendicular to the first axis. The adverbs "axially" and "radially" refer to the axial and radial direction, respectively.

In an exemplary embodiment, the retainer is configured to be disposed around the connection head, i.e. the retaining members collectively forming the retainer can be mounted on the connection head, so as to form a first assembly, the first assembly having a first cross-sectional dimension smaller than the first opening i.e. than the minimum cross-sectional dimension of the first opening, so that the first assembly is loadable into the receiver by passing through the first opening i.e. the connection head and all the retaining members are loadable at once into the receiver. In other words, the retainer may have a non-extended or compact configuration in which it can be passed through the first opening to be bottom-loaded, together with the connection head, into the receiver, and an extended configuration in which it cannot be passed through the first opening. Typically, the retainer comprises two discrete retaining members. However, it is foreseen that the retainer may be made up of more than two retaining members, each matable with both the connection head, on the radially inner side of the retaining member, and the seating surface of the receiver on the radially outer side of the retaining member. The retaining members may be identical or mirror images of one another but may also be of varying sizes.

In certain embodiments, when assembling the retaining members with the connection head, the inner surfaces of the retaining members fit on the outer surface of the connection head and, in particular, on the lower portion of the outer surface. The resulting assembly, i.e. the above-mentioned first assembly, has, in a compact configuration, a smaller outer cross-sectional dimension than the cross-sectional dimension of the first opening of the receiver. This allows the first assembly, in its compact configuration, to be bottom-loaded into the receiver, through the first opening. Once loaded into the receiver, the first assembly is extended: the retaining members fit in the seating surface and are spaced apart in the circumferential direction, i.e. they cover less than 360° around the connection head, thus leaving at least one circumferential gap between them. The pin(s) of the insert is (are) adapted to fit into the gap(s) between the retaining members so as to force the retaining members apart from each other and towards the receiver cavity walls, thus securing the retaining members inside the cavity. The retaining members, in turn, will, in one embodiment, in the extended state, essentially provide a constriction of the first opening, i.e. provide a lower retainer opening—hereafter called "retaining opening" or "third opening"—confined by a lower edge, which is dimensioned such that the connection head does not fit through the retaining opening, i.e. the cross-sectional dimension of the retaining opening is smaller than that of the connection head. This allows the connection head to be captured within the receiver cavity, while the bone anchoring part of the anchor either is provided with a necking adjacent the connection head which fits through the retaining opening or it fits through the retaining opening in its entirety, e.g. when the bone anchoring part is a threaded shank, at least the core of a thread is smaller than the retaining opening. In an embodiment the section of the anchor adjacent the connection head has play within the retaining opening. This allows the anchor to be pivoted with the connection head captured inside the receiver provided that the connection head and the inner geometry of the retainer are appropriately shaped, e.g. one of them has a spherical section in their mutual contact region.

In certain embodiments, the lower surface of the main body of the insert is configured to frictionally engage the connection head, i.e. to exert a force on the connection head which is thus clamped between the insert and the lower edge of the retainer. The lower surface of the main body may be dimensioned to be inserted into an upper opening of the retainer and, in particular, between the connection head and the retainer in its extended configuration. Opposite to the lower surface, the upper surface of the main body may define a seat or saddle being sized and shaped to closely receive the support member. In operation, a substantial portion of the seat or saddle may frictionally engage an outer surface of the support member.

In certain embodiments, the main body has a lower edge configured for insertion between the retainer and the connection head. The lower edge may act like a wedge which moves the retaining members of the retainer and the connection head apart from each other, i.e. which moves the retainer towards the extended configuration, thereby radially enlarging or extending the retainer cross-sectional dimension and thus preventing the retainer from disengaging from the receiver.

In certain embodiments, the lower edge of the insert is configured to circumferentially surround the connection head, at least partially, and has a funnel-shaped or tapered inner surface (pointing upwards). For instance, the thickness of the lower edge may decrease as the distance from the main body of the insert increases. When the insert urges the connection head, the inner surface of the lower edge frictionally engages the connection head. The inner surface of the lower edge then holds the connection head in a taper lock type connection due to its tapered shape.

In certain embodiments, the pin protrudes axially outwardly or downward from the main body. Thus, the pin engages between the retaining members before the lower surface of the main body engages between the retainer and the connection head.

In certain embodiments, the pin protrudes laterally from the main body. In particular, the pin may protrude radially outwardly from the main body.

Each retaining member has radially inner and outer surfaces, the inner surface being configured to be, at least in certain regions, in contact with the connection head of the anchor and the outer surface being configured to engage with the seating surface of the cavity. In other words, the retainer members are adapted to fit on the seating surface and to collectively provide a kind of collar about the connection head. In certain embodiments, when fitted on the seating surface, the retaining members form a retaining cavity in which the connection head fits and a retaining opening, or third opening, at a lower end of the retaining cavity, the third opening having a cross-sectional dimension smaller than the maximum cross-sectional dimension of the connection head so as to maintain the head inside the retaining cavity and impede the head movement in the direction from top to bottom.

In certain embodiments, the connection head is substantially spherically shaped or, to be more precise, a spherical segment, and the inner surfaces of the retaining members collectively define a substantially spherically shaped socket for the connection head, thereby forming a ball-and-socket type connection between the anchor and the receiver. This allows rotation of the receiver about the anchor until a desired relative rotational position of the receiver and the anchor is achieved. In other words, an angular relationship between an axis of the anchor and an axis of the receiver, more particularly an axis of the receiver extending through the first opening, or the first axis, may be varied. To this extent it is advantageous if the anchor shank is formed such that a portion of the shank adjacent the connection head has play in the retaining opening. Thus, the retaining members, which may move with the receiver, may also rotate relative to the head of the anchor until a desired rotational position is achieved.

In certain embodiments, the receiver top portion is hollow and defines a first internal passage communicating with the cavity, the insert being movable within the first internal passage. The first internal passage may be configured such that the insert is radially guided within the passage and axially moveable within the passage, along the first axis. The first internal passage may communicate with the exterior of the receiver through a second opening at an upper end of the receiver. The insert may be top-loaded into the receiver through the second opening.

In certain embodiments, the device further comprises a locking member engageable with the receiver, for urging the insert, either directly or indirectly through the support member placed therebetween, in a locking direction, i.e. from top to bottom, to frictionally lock the position of the outer surfaces of the retaining members relative to the seating surface and, eventually, to frictionally lock the anchor in position with respect to the receiver. For instance, the receiver may be provided with a thread configured to mate under rotation with another thread provided on the locking member, so that the locking member can be engaged with and moved relative to the receiver so as to urge, directly or indirectly, the insert towards the bottom of the receiver, and/or exert a force on the insert.

In certain embodiments, the device further comprises a fastening system for fastening a support member to the receiver. The support member may be an elongate member such as a rod. The fastening system may comprise the locking member and the receiver, the support member being clamped between these parts. For urging the insert in the locking direction, the locking member may push the support member which, in turn, pushes the insert.

In certain embodiments, the connection head of the anchor has a tool engagement profile adapted for non-slip engagement by a tool for driving the anchor into a bone. The tool engagement profile may be an inner profile for engaging a driving tool for both driving and rotating the anchor body into a bone. Many different shaped drives and cooperating tools are possible, such as hex-shaped, grooved, multi-lobular, etc.

In certain embodiments, the anchor, the receiver, the retainer and the insert are preassembled. Thus, the practitioner, or other operative, is provided with a preassembled device before surgical implantation. The receiver top portion may be provided with an internal flange or shoulder inside the first internal passage, the insert abutting against the internal flange or shoulder when the device is preassembled. The internal flange or shoulder may prevent the insert from disengaging from the receiver after assembly.

According to another aspect of the present disclosure, there is provided a method for assembling a bone anchoring device according to the present disclosure, wherein the retainer is disposed around the connection head so as to form a first assembly, the first assembly being bottom-loaded into the receiver by passing through the first opening, wherein the insert is top-loaded into the receiver, and wherein the retaining members of the receiver are circumferentially spaced apart from each other by inserting said pin(s) therebetween.

According to another aspect of the present disclosure, there is provided a stabilization system for stabilizing at least two vertebrae, the system comprising: a first anchoring device configured to be fastened to a first vertebra, a second anchoring device configured to be fastened to a second vertebra, and a support member for connecting the first and second anchors together, thereby providing stabilization between the first and second vertebrae, wherein at least the first anchoring device is a bone anchoring device according to the present disclosure. The second anchoring device may be similar to or different from the first anchoring device. The support member may be rigid or it may have elastic properties. The support member may be, for instance, a rod.

According to another aspect of the present disclosure, there is provided a method for connecting a bone, e.g. a vertebra, to a support member, comprising the steps of:

providing a support member and a bone anchoring device as described above, impeding relative movement between the bone anchoring device and a bone, by fixing the bone anchoring part to the bone, and impeding relative movement between the bone anchoring device and the support member, by fastening the receiver to the support member.

Such a method has the advantages derived from using a bone anchoring device according to the present disclosure.

Other features and advantages of the invention will become apparent from the following detailed description, taken in conjunction with the accompanying drawings, which illustrate, by way of example, the principles of the invention.

BRIEF DESCRIPTION OF THE DRAWINGS

In the drawings, like reference signs generally refer to the same parts throughout the different views.

The drawings are not necessarily to scale, emphasis instead generally being placed upon illustrating the principles of the invention.

DETAILED DESCRIPTION

In the following detailed description, it is referred to the accompanying drawings showing an example of bone anchoring device. It is intended that this example be considered as illustrative only, the scope of the invention not being limited to this example.

To avoid detail not necessary to enable those skilled in the art to practice the invention, the description may omit certain information known to those skilled in the art.

It is also noted that any reference to the words top, bottom, up and down, and the like, in the present disclosure refers to the orientation shown in the various drawings, as well as the normal connotations of these words when applied to a bone anchoring device, and is not intended to restrict positioning of the device in actual use. It should be noted, moreover, that this complies with the use of the words in the art, referring e.g. to "top loading pedicle screws", where skilled persons use "top" as a synonym for the head of a screw, i.e. the receiver in this case, or, in other words, for the proximal side, i.e. the side which is intended to be directed towards the surgeon during surgery. As a matter of course "bottom" then designates the opposite side.

Figure 2:
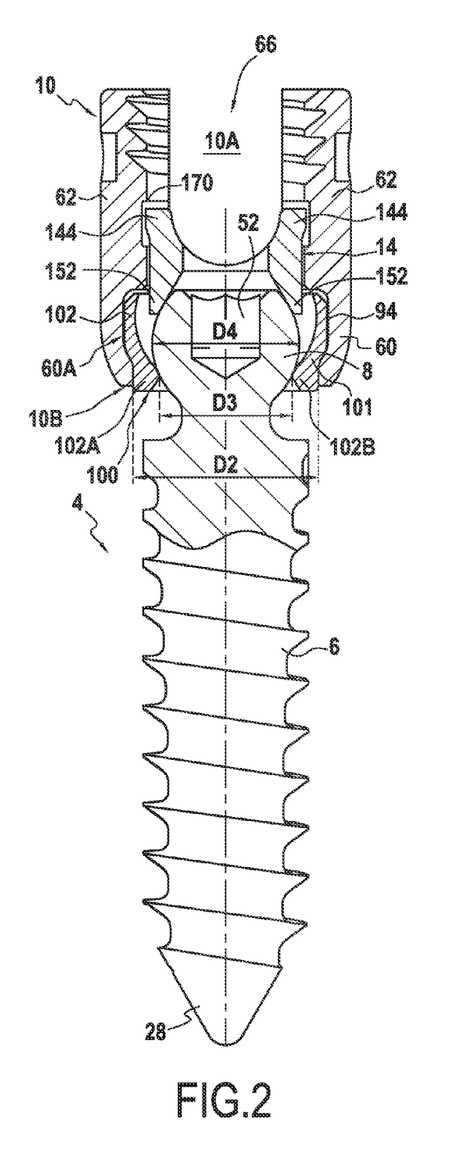
FIG. 2 is a sectional view of the device of FIG. 1 (without the locking member and support member) along axial plane II-II.
Figure 3:
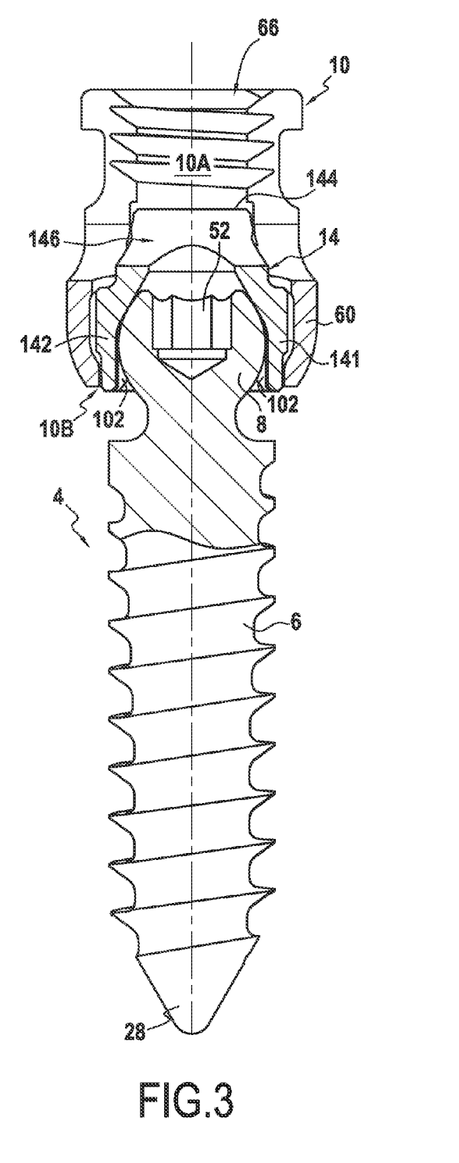
FIG. 3 is a sectional view of the device of FIG. 1 (without the locking member and support member) along axial plane III-III.
Figure 4:
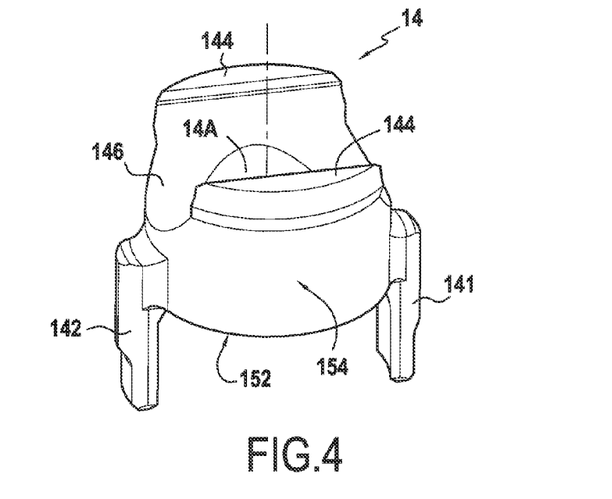
FIG. 4 is an enlarged view of the insert of FIG. 1.

With reference to the figures, the reference number 1 generally designates a bone anchoring device being, in this example, a polyaxial bone screw. The device 1 includes: an anchor 4 comprising a threaded shank 6 as an example of a bone anchoring part, and an upwardly extending upper portion, or connection head 8, being integral with the shank 6; a receiver 10; a multi-piece retainer 12 and an insert 14. The multi-piece retainer is depicted as a two-piece retainer 12. The anchor 4, receiver 10, retainer 12 and insert 14 are preferably preassembled as shown in FIGS. 2 and 3, prior to implantation of the shank 6 into a bone such as a vertebra (not shown).

Figure 1:
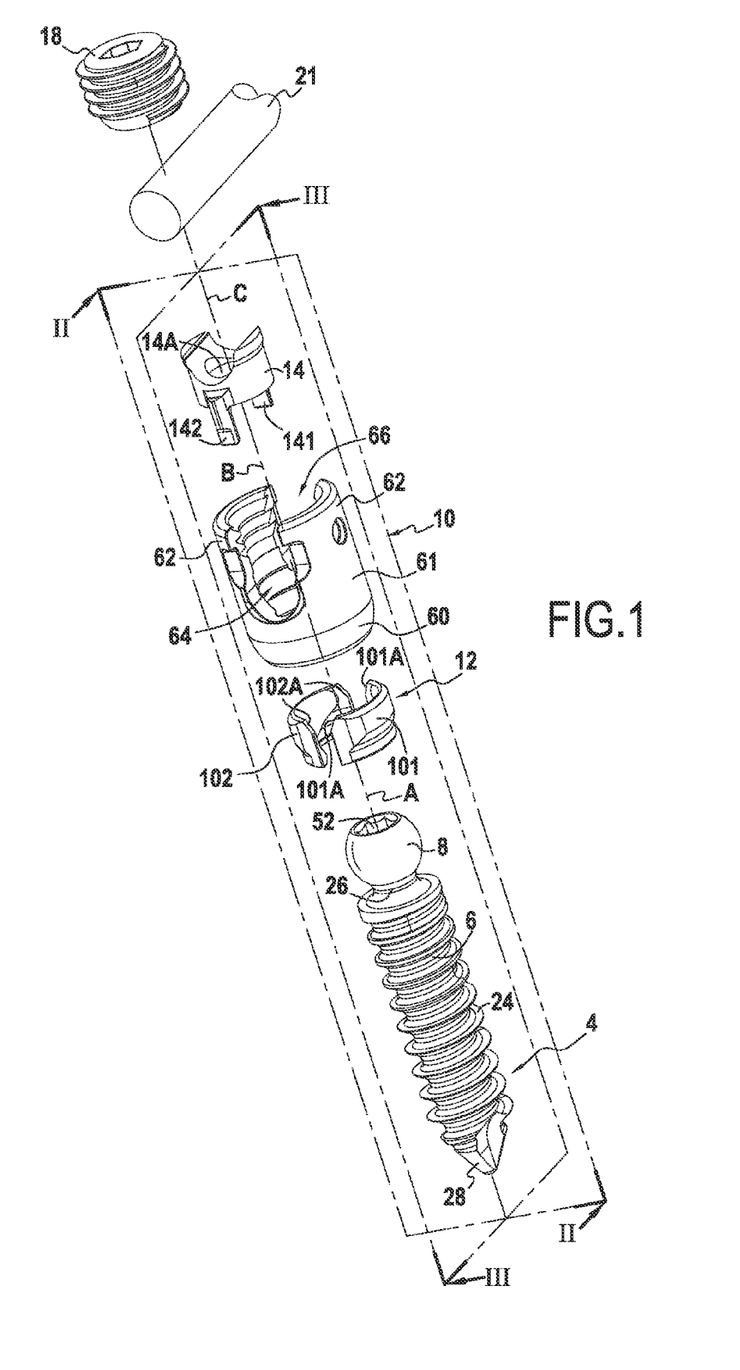
FIG. 1 is an exploded perspective view of an example of a bone anchoring device including an anchor, a receiver, a two-piece retainer, an insert and a locking member, further shown with a longitudinal support member.

FIG. 1 further shows a locking member 18 for pressing a longitudinal member such as a rod 21 against the insert 14 which, in turn, frictionally engages the connection head 8 with a compressive force between the insert and the lower edge of the retainer 12, so as to fix the rod 21 relative to the shank 6, and thus to the vertebra. The retainer 12 is disposed between the connection head 8 and the lower portion, or base 60, of the receiver 10. The receiver 10 and the anchor 4 cooperate, via the retainer 12, in such a manner that relative movement, e.g. pivotable movement, between the anchor 4 and the receiver 10 is enabled until both are locked or fixed relative to each other, near the end of an implantation procedure. In other words, the head 8 of the anchor 4 may pivot relative to the retainer 12 within the receiver 10 prior to locking the receiver 10 to the anchor 4, which in turn is achieved by locking the locking member 18, which urges the rod 21 towards the insert 14, the insert 14 frictionally engaging the connection head 8. The receiver 10 and the anchor 4 can be secured at any of a plurality of positions relative to one another and within a selected range of angles between anchor axis A and receiver axis B.

The anchor 4 is elongate, with the shank 6 having a helically wound thread 24 extending from near a neck 26 located adjacent to the connection head 8, to a tip 28 of the shank 6. The connection head 8 is configured for connecting the shank 6 to the receiver 10 by being captured in the retainer 12 and the receiver 10. In this example, the head 8 is substantially spherical. A tool engagement structure or inner drive 52 is provided in the top surface of the head 8. The illustrated inner drive 52 is a multi-lobular cavity for engaging a driving tool (not shown) for both driving and rotating the shank body 6 about its axis A, into a bone.

The receiver 10 has a hollow top portion 61 with a first internal passage 10A being partially cylindrical around an axis B, and a base 60 with an inner seating surface defining a cavity 60A. The cavity 60A communicates, on its upper side, with the first internal passage 10A and, on its lower side, with the exterior of the receiver 10 through a first opening 10B at a lower or bottom surface of the receiver 10. The receiver 10 is rotatable around axis B which is shown in FIG. 1 as being aligned with the rotation axis A of the shank 6, such orientation being desirable during assembly of the receiver 10 with the anchor 4 (see FIG. 6). After the receiver 10 is pivotally attached to the anchor 4, and the anchor 4 is implanted in a vertebra (not shown), axis B is typically disposed at an angle with respect to axis A.

The receiver top portion 61 is generally U-shaped. The top portion 61 comprises a pair of opposed upstanding arms 62 integral with the base 60 and forming a cradle and defining a U-shaped channel 64 between the arms 62 with an upper opening 66. The channel 64 has a width for operably snugly receiving the rod 21 between the arms 62. Each of the arms 62 has an interior surface that defines the first internal passage 10A and is provided with an inner thread configured to mate under rotation with an outer thread provided on the locking member 18, so that the locking member 18 can be inserted and advanced into the first internal passage 10A, between the arms 62.

Figure 5:
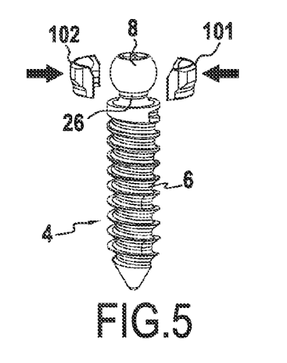
FIGS. 5 to 7 illustrate different steps of the assembly of the anchor with the two-piece retainer, the receiver and the insert, leading to the assembled device shown in FIGS. 2 and 3.
Figure 6:
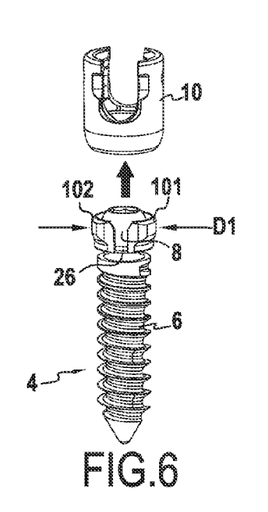

The retainer 12 is used to retain the head 8 of the anchor 4 within the receiver 10 and articulate the shank 6 with respect to the receiver 10. The retainer 12 is made of multiple discrete pieces, or retaining members 101, 102, which are each sized and shaped to engage the head 8 while being engaged with a seating surface 94 of the receiver base 60 (see FIG. 2). In some instances, the retaining members may be considered shells. In the illustrative embodiment, the retainer 12 is formed of two discrete pieces, a first retaining member 101 and an opposingly positioned second retaining member 102. However, in other instances the retainer 12 may include three, four, or more discrete pieces. In this example, the second retaining member 102 is identical to the first retaining member 101. The retaining members 101, 102 collectively provide a collar about the head 8. The inner surfaces of the retaining members 101, 102 may be complementary to the lower portion of the outer surface of the head 8. When assembling the retaining members 101, 102 with the head 8, the retaining members 101, 102 mate with the lower portion of the head 8, just above the neck 26, as shown in FIGS. 5-6. The resulting assembly in a compact configuration has a cross-section with an outer diameter D1 (see FIG. 6) smaller than the inner diameter D2 (see FIG. 2) of the first opening 10B of the receiver 10. This allows the assembly to be bottom-loaded into the receiver 10, through the first opening 10A, as illustrated in FIG. 6.

In this example, the retaining members 101, 102 are not in contact with each other when fully installed around the head 8, as shown in FIG. 6. In other words, the retaining members 101, 102 only partially circumferentially surround the head 8 when fully installed around the head 8, leaving a gap between adjacent retaining members around the circumference of the head 8. In other examples (not shown), the retaining members 101, 102 may be in contact with each other when fully installed around the head 8. In any case, however, the retaining members 101, 102 are not in contact with each other when captured within the receiver 10, between the connection head 8 and the seating surface 94, since the retaining members 101, 102 are spaced apart by the pins 141, 142 of the insert 14, as explained below.

Figure 7:
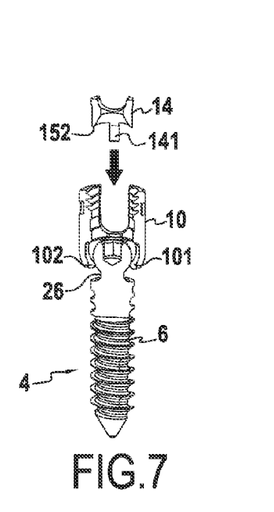

With particular reference to FIGS. 1, 3, 4 and 7, the insert 14 is sized and shaped to be received by and top-loaded into the receiver 10 through the upper opening 66. In operation, the insert 14 is disposed between the rod 21 and the head 8 as illustrated in FIG. 7.

The insert 14 has an operational central axis C that is the same as the central axis B of the receiver 10. The insert 14 has a central channel or through bore 14A. The through bore 14A is sized and shaped to receive a driving tool (not shown) therethrough, this tool engaging the inner drive 52 when the shank body 6 is driven into bone. The insert 14 comprises a main body 154 including a pair of upwardly extending arms 144 with a U-shaped surface or saddle 146 formed therebetween. The saddle 146 is sized and shaped to closely receive the cylindrical rod 21 or other longitudinal support member. In operation, a substantial portion of the saddle 146 frictionally engages an outer surface of the rod 21.

Opposite to the saddle 146, the insert 14 has a lower circular edge 152 circumferentially surrounding the through bore 14A. The lower edge 152 has a tapered inner surface. In this example, the radial thickness of the lower edge 152 decreases as the distance from the saddle 146 increases (see FIGS. 2 and 7). The main body 154 has a substantially cylindrical outer surface of axis C extending between the saddle 146 and the lower edge 152.

The insert 14 also includes one or more, or a plurality of legs or pins 141, 142 protruding from the main body 154. In the illustrative embodiment, the insert 14 comprises two legs or pins 141, 142, on opposite sides of the main body 154. The pins 141, 142 are diametrically opposed and symmetrical with respect to the main body 154. The pins 141, 142 may protrude laterally—e.g. radially—outwardly from the main body 154. In other words, the circle circumscribing the pins 141, 142 has a diameter greater than the diameter of the cylindrical main body 154. The pins 141, 142 may additionally or alternatively protrude downward from the lower edge 152, i.e. it may protrude axially outwardly towards the anchor. In other words, the distal end of the pins 141, 142 is further away from the saddle 146 than the lower edge 152.

As illustrated in FIG. 7, when the connection head 8 and the retaining members 101, 102 are disposed within the receiver 10 e.g., bottom-loaded, and when the connection insert 14 is top-loaded into the receiver 10, the pins 141, 142 are inserted between the retaining members 101, 102 and, therefore, the retaining members 101, 102 are circumferentially spaced apart from one another to an extended configuration, i.e. the outer diameter D1 of the retainer cross-section increases. In this example, in the extended configuration, the retaining members fit in the cavity 60A and the outer diameter D1 of the retainer cross-sectional dimension in the extended configuration is greater than the inner diameter D2 of the first opening 10B of the receiver 10, thus preventing the retainer 12 from being removed from the first opening 10B of the receiver 10. Thus, relative movement between the retaining members 101, 102 is prevented and a tighter fit of the retaining members 101, 102 in the receiver cavity 60A is obtained, which improves the mechanical behavior of the retaining members 101, 102 and reduces the risk that the retaining members 101, 102 will disengage from the receiver 10. Also, in the extended configuration (see FIG. 2), lower edges 102A, 102B of the retaining members 101, 102 collectively define a third opening 100 having a minimum cross-sectional dimension, i.e., in this example, a minimum diameter smaller than the maximum cross-sectional dimension or diameter of the anchor head 8, thereby preventing the head 8 from being removed from the retainer 12. In the illustrative example, the third opening 100 is circular and has a diameter D3. The diameter D3 is smaller than the maximum diameter D4 of the head 8 (see FIG. 2). Thus, in the extended configuration, the retainer 12 and the head 8 are prevented from being removed from the receiver 10 through the first opening 10B.

In order to make the insertion of the pins 141, 142 between the retaining members 101, 102 easier, the upper corners 101A, 102A of the retaining members 101, 102 are beveled, as shown in FIG. 1. As the pins 141, 142 are positioned between the retaining members 101, 102, a first side of the first pin 141 may contact a first edge of the first retaining member 101 while a second side of the first pin 141 may contact a first edge of the second retaining member 102. Similarly, a first side of the second pin 142 may contact a second edge of the first retaining member 101 while a second side of the second pin 142 may contact a second edge of the second retaining member 102. Furthermore, the lower edge 152 of the main body 154 of the insert 14 may be positioned radially inward of the retaining members 101, 102 such that an upper portion of the retaining members 101, 102 radially surround the lower edge 152 of the main body 154.

When the insert 14 is inserted into the receiver 10, it is forced through the first internal passage 10A, beyond an internal flange or shoulder 170 provided inside the passage 10A (see FIG. 2). Thus, after insertion, the insert 14 is prevented from disengaging from the receiver 10 by abutting against the internal shoulder 170.

After having inserted the connection insert 14 into the receiver 10 (this insertion step being illustrated in FIG. 7) the assembled device of FIGS. 2-3 is obtained. The practitioner or other operative may be provided with this preassembled device before surgical implantation. Then, the rod 21 and the locking member 18 are positioned and the locking member 18 is tightened for pressing upon the rod 21. When the locking member 18 presses upon the rod 21, the rod 21 operatively presses upon the insert 14 that, in turn, presses upon the connection head 8, that in turn presses against the retaining members 101, 102 that in turn press against the seating surface 94 of the receiver 10, resulting in ultimate frictional engagement and locking of the angular position of the anchor 4 with respect to the receiver 10. When the insert 14 urges the connection head 8, the inner surface of the lower edge 152 frictionally engages the connection head 8. The lower edge 152 may also act like a wedge separating the retaining members 101, 102 of the retainer 12 and the head 8, thereby further extending the retainer cross-sectional dimension for a tighter fit in the receiver cavity 60A.

The invention claimed is:

1. A bone anchoring device comprising:
   an anchor comprising a connection head and a bone anchoring part for fixation to a bone;
   a receiver having a top portion and a base, the base having a seating surface defining a cavity, the cavity communicating with an exterior of the receiver through a first opening at a lower end of the receiver, the first opening being configured to receive the connection head therethrough;
   a multi-piece retainer comprising at least two discrete retaining members unattached to each other, the retaining members being configured to engage with the receiver seating surface while a surface of each of the retaining members frictionally engages the connection head; and
   an insert disposed within the receiver, the insert comprising a main body configured to frictionally engage the connection head;
   wherein the insert comprises at least one pin protruding from the main body, each pin being configured for circumferential insertion between two adjacent unattached retaining members of the retainer, so as to hold the retaining members circumferentially spaced apart from each other, thus securing the retaining members inside the cavity.

2. The bone anchoring device of claim 1, wherein the retainer is configured to be disposed around the connection head so as to form a first assembly, the first assembly having a first cross-sectional dimension smaller than the first opening, so that the first assembly is loadable into the receiver by passing through the first opening.

3. The bone anchoring device of claim 1, wherein the main body of the insert has a lower edge configured for insertion between the retaining members and the connection head.

4. The bone anchoring device of claim 1, wherein a lower edge of the insert is configured to circumferentially surround the connection head, at least partially, and has a tapered inner surface.

5. The bone anchoring device of claim 1, wherein the at least one pin protrudes downward from the main body.

6. The bone anchoring device claim 1, wherein the at least one pin protrudes laterally outwardly from the main body.

7. The bone anchoring device of claim 1, wherein each retaining member has inner and outer surfaces, the inner surface being configured to be in contact with the connection head and the outer surface being configured to engage with the seating surface, wherein the connection head is substantially spherical and wherein the inner surfaces of the retaining members define a socket for the connection head, thereby forming a ball-and-socket type connection between the anchor and the receiver.

8. The bone anchoring device of claim 1, wherein the receiver top portion is hollow and defines a first internal passage communicating with the cavity, the insert being movable within the first internal passage.

9. The bone anchoring device of claim 1, further comprising a fastening system for fastening a support member to the receiver.

10. The bone anchoring device of claim 1, wherein the retainer comprises two retaining members and the insert comprises two pins on opposite sides of its main body.

11. The bone anchoring device of claim 1, wherein the bone anchoring part is a threaded shank.

12. The bone anchoring device of claim 1, further comprising a locking member engageable with the receiver for urging the insert in a locking direction to frictionally lock the position of the outer surfaces of the retainer members relative to the seating surface, and to frictionally lock the position of the anchor with respect to the receiver.

13. The bone anchoring device of claim 1, wherein the receiver top portion is hollow and defines a first internal passage communicating with the cavity and is provided with an internal flange or shoulder inside the first internal passage, and wherein the insert abuts against the internal flange or shoulder when the anchor, the receiver, the retainer and the insert are preassembled.

14. A method for connecting a bone to a support member, comprising the steps of:
  impeding relative movement between a bone anchoring device and a bone, by fixing the bone anchoring device to the bone, the bone anchoring device comprising:
    an anchor comprising a connection head and a bone anchoring part for fixation to a bone;
    a receiver having a top portion and a base, the base having a seating surface defining a cavity, the cavity communicating with the exterior of the receiver through a first opening at a lower end of the receiver, the first opening being configured to receive the connection head therethrough;
    a multi-piece retainer comprising at least two discrete retaining members unattached to each other, the retaining members being configured to engage with the receiver seating surface when they are captured between the connection head and the seating surface; and
    an insert disposed within the receiver, the insert comprising a main body configured to frictionally engage the connection head;
    wherein the insert comprises at least one pin protruding from the main body, each pin being configured for circumferential insertion between two adjacent unattached retaining members of the retainer, so as to hold the retaining members circumferentially spaced apart from each other, thus securing the retaining members inside the cavity; and
  impeding relative movement between the bone anchoring device and a support member, by fastening the receiver to the support member.

15. A method for assembling a bone anchoring device comprising:
  disposing a retainer around a connection head of an anchor so as to form a first assembly, the retainer comprising at least two discrete retaining members;
  bottom-loading the first assembly into a receiver by passing the first assembly through a first opening of the receiver located at a lower end of the receiver;
  top-loading an insert into a cavity of the receiver from a top end of the receiver opposite the lower end, the insert comprising a main body configured to frictionally engage the connection head of the anchor and at least one pin protruding from the main body; and
  inserting the pin(s) between the retaining members of the retainer such that the retaining members are circumferentially spaced apart from each other by inserting the pin(s) therebetween.

16. A bone anchoring device comprising:
  an anchor comprising a connection head and a bone anchoring part for fixation to a bone;
  a receiver having a top portion and a base, the base having a seating surface defining a cavity, the cavity communicating with the exterior of the receiver through a first opening extending through the base of the receiver, the first opening being configured to receive the connection head therethrough;
  a multi-piece retainer shiftable between a compact configuration and an extended configuration, the retainer comprising a first retaining member and a second retaining member each configured to engage the connection head; and
  an insert disposed within the receiver, the insert comprising a main body configured to frictionally engage the connection head, a first pin, and a second pin spaced apart from the first pin, the first pin and the second pin each protruding from the main body;
  wherein the first retaining member and the second retaining member are engaged with the connection head and have a maximum outer extent smaller than an inner diameter of the first opening in the compact configuration;
  wherein the first pin is configured to contact the first retaining member and the second retaining member, and the second pin is configured to contact the first retaining member and the second retaining member, the first pin and the second pin urging the first and second retaining members apart from each other and into engagement with the receiver seating surface in the extended configuration.

17. The bone anchoring device of claim 16, wherein in the extended configuration, the first pin and the second pin are each disposed radially outward of the connection head between the first retaining member and the second retaining member.

18. The bone anchoring device of claim 16, wherein the insert further includes a U-shaped saddle and pair of arms extending upwardly therefrom configured to receive a longitudinal support member.

19. The bone anchoring device of claim 18, wherein the receiver includes internal threads configured to engage a threaded locking member for pressing the longitudinal support member against the insert.

20. A bone anchoring device comprising:
- an anchor comprising a connection head and a bone anchoring part for fixation to a bone;
- a receiver having a top portion and a base, the base having a seating surface defining a cavity, the cavity communicating with an exterior of the receiver through a first opening at a lower end of the receiver, the first opening being configured to receive the connection head therethrough;
- a multi-piece retainer comprising at least two discrete retaining members unattached to each other, the retaining members being configured to engage with the receiver seating surface when they are captured between the connection head and the seating surface; and
- an insert disposed within the receiver, the insert comprising a main body configured to frictionally engage the connection head;
- wherein the insert comprises at least one pin protruding from the main body,
- wherein the at least one pin protrudes downward from the main body, each pin being configured for circumferential insertion between two adjacent unattached retaining members of the retainer, so as to hold the retaining members circumferentially spaced apart from each other, thus securing the retaining members inside the cavity.

21. A bone anchoring device comprising:
- an anchor comprising a connection head and a bone anchoring part for fixation to a bone;
- a receiver having a top portion and a base, the base having a seating surface defining a cavity, the cavity communicating with an exterior of the receiver through a first opening at a lower end of the receiver, the first opening being configured to receive the connection head therethrough;
- a multi-piece retainer comprising at least two discrete retaining members unattached to each other,
- wherein each retaining member has inner and outer surfaces, the inner surface being configured to be in contact with the connection head and the outer surface being configured to engage with the seating surface, wherein the connection head is substantially spherical and wherein the inner surfaces of the retaining members define a socket for the connection head, thereby forming a ball-and-socket type connection between the anchor and the receiver, the retaining members being configured to engage with the receiver seating surface when they are captured between the connection head and the seating surface; and
- an insert disposed within the receiver, the insert comprising a main body configured to frictionally engage the connection head;
- wherein the insert comprises at least one pin protruding from the main body, each pin being configured for circumferential insertion between two adjacent unattached retaining members of the retainer, so as to hold the retaining members circumferentially spaced apart from each other, thus securing the retaining members inside the cavity.

* * * * *